(12) United States Patent
Gieselmann et al.

(10) Patent No.: US 8,979,533 B2
(45) Date of Patent: Mar. 17, 2015

(54) DENTAL IMPLANT

(75) Inventors: Dirk-Rolf Gieselmann, Zurich (CH);
Harald Ceschinski, Bochum (DE)

(73) Assignee: MDI Dental—Und Implantattechnik GmbH, Duisburg (DE)

( * ) Notice: Subject to any disclaimer, the term of this patent is extended or adjusted under 35 U.S.C. 154(b) by 84 days.

(21) Appl. No.: 12/532,250

(22) PCT Filed: Mar. 15, 2008

(86) PCT No.: PCT/EP2008/002089
§ 371 (c)(1),
(2), (4) Date: Apr. 15, 2010

(87) PCT Pub. No.: WO2008/113532
PCT Pub. Date: Sep. 25, 2008

(65) Prior Publication Data
US 2011/0053115 A1    Mar. 3, 2011

(30) Foreign Application Priority Data

Mar. 19, 2007 (DE) .......................... 10 2007 013 703

(51) Int. Cl.
*A61C 8/00* (2006.01)

(52) U.S. Cl.
CPC ............... *A61C 8/005* (2013.01); *A61C 8/0086* (2013.01)
USPC .......................................................... 433/174

(58) Field of Classification Search
CPC .......... A61C 8/005; A61C 8/0086; A61C 8/00
USPC ........................ 433/172–174, 201.1, 175, 176
See application file for complete search history.

(56) References Cited

U.S. PATENT DOCUMENTS

| 4,756,689 | A | * | 7/1988 | Lundgren et al. | ............ | 433/173 |
| 4,824,372 | A | * | 4/1989 | Jorneus et al. | ................ | 433/174 |
| 5,145,371 | A | * | 9/1992 | Jorneus | .......................... | 433/173 |
| 5,702,252 | A | * | 12/1997 | Rogers et al. | .................. | 433/173 |
| 5,989,028 | A | * | 11/1999 | Niznick | ........................ | 433/173 |
| 6,305,938 | B1 | * | 10/2001 | Br.ang.nemark | ............ | 433/173 |
| 7,883,336 | B2 | * | 2/2011 | Hansson | ....................... | 433/173 |
| 2005/0164146 | A1 | * | 7/2005 | Cantor | .......................... | 433/173 |
| 2006/0020346 | A1 | * | 1/2006 | Hunter et al. | .............. | 623/23.51 |

* cited by examiner

*Primary Examiner* — Cris L Rodriguez
*Assistant Examiner* — Mirayada A Aponte
(74) *Attorney, Agent, or Firm* — Berliner & Associates

(57) ABSTRACT

The invention relates to an implant for anchoring a prosthesis in the jaw of a patient, having a base body (1) and a post (2) connecting to the top thereof, wherein the post (2) engages with a recess opening (3) of the base body (1) in a positive and non-positive manner and can be firmly connected thereto. In order to improve such an implant, the invention suggests that a sealing collar (4) surrounding the recess opening (3), and an annular groove (5) surrounding the sealing collar (4) be provided on the top of the base body (1), wherein the post (2) has a circumferential shoulder (6) on the bottom thereof facing the base body (1), the shoulder having a shape that is complementary to the sealing collar (4) and the annular groove (5).

8 Claims, 2 Drawing Sheets

DENTAL IMPLANT

BACKGROUND OF THE INVENTION

1. Field of the Invention

The invention relates to an implant for anchoring a prosthesis in the jaw of a patient, having a base body and a post connecting to the top thereof, wherein the post engages with a recess opening of the base body in a positive and non-positive manner and can be firmly connected thereto.

2. Description of the Related Art

Where one or several natural teeth need to be replaced, dental implants, which are a means for anchoring dental replacements, such as crowns, bridges or prostheses, are nowadays used in dental medicine. Dental implants within this meaning are pillars which are anchored in the jawbone and function as artificial tooth roots. They are firmly anchored elements which are implanted in the jawbone. They enable individual teeth and dental bridges to be fixed in place without disturbing healthy neighboring teeth. Implantation is a process in which dental implants are firmly anchored by pressing or screwing them into a tooth root cavity previously formed in the jawbone. The implant usually consists of several parts, namely a base body, which forms the anchor proper, a post, which engages with the base body and carries the crown or bridge or prosthesis, and a fixing element which serves to secure the post to the base body.

In a widely used type of implant, the post is fixed in the recess of the base body by means of a fixing screw which runs through the hollow post. In this configuration, the post is provided, for instance, with a hexagonal section facing the base body, which fits accurately into the hexagonal contour of the recess opening of the base body. In the area of its contact faces with the base body, the post is additionally provided with a shoulder which interacts with a matching end the on top of the base body. Here, the objective is to obtain a connection that is as gap-free as possible between the base body and the post to prevent the ingress of bacteria. Such a gap-free interface is generally considered necessary in order to avoid the undesired consequences of an implantation—so-called perioimplantitis. Perioimplantitis may lead to the implant losing its anchor from the jawbone.

Several dental implants with gap-free interfaces are known in the prior art. The known dental implants are partly not satisfactory in terms of resistance to the significant pressures that teeth are subjected to. If the connection between the post and the base body is not perfect, the implant may suffer damage which may lead to micromovements, cause the post to become loose or even damage the base body, so that the implant may lose its functionality in the medium term. If the connection between the post and the base body becomes loose, this may permit bacteria to enter the developing gap between the base body and the post, which may result in the afore-mentioned perioimplantitis.

SUMMARY OF THE INVENTION

In view of this background, the objective of the invention is to provide a dental implant that is improved over the prior art.

Starting from the implant of the type mentioned at the outset, the invention solves this task by providing, on the top of the base body, a sealing collar surrounding the recess opening and annular groove surrounding the sealing collar, wherein the post has a circumferential shoulder on the bottom thereof facing the base body, which shoulder has a shape that is complementary to the sealing collar and the annular groove.

The design of the base body, which is provided, at its top, with a sealing collar and an annular groove surrounding that sealing collar, offers the advantage of maximizing the contact face between the post and the base body. The contact face is made up of surface sections that run parallel and transversely to the longitudinal direction of the implant. Due to the size of the contact face, the connection between the post and the base body is especially tight. The design featuring a sealing collar and an annular groove extends the distance from the outside of the implant to its inner space, which makes it more difficult for microorganisms to enter the implant and for bacteria to develop and grow inside the hollow spaces of the implant. In this manner, the risk of perioimplantitis is significantly reduced.

In addition, the design of the implant as covered by the invention, which features a sealing collar and an annular groove, permits the connection between the base body and the post to be made particularly strong, so that it can withstand the forces acting during chewing on the implant in both radial and axial direction without the risk of damage to the implant. Here, it is essential that the post according to the invention has, at its bottom end facing the base body, a shape that is complementary to that of the base body provided with the sealing collar and the annular groove. Complementary means that the two interacting parts—base body and post—engage positively with each other.

In a preferred embodiment of the implant according to the invention, the sealing collar, when viewing in the longitudinal direction of the implant, is web-shaped in cross section and has an axially extending inner wall and an outer wall that is essentially parallel to the former. This design of the sealing collar contributes to the fact that the connection between the base body and the post is particularly resistant to radial loads and shear forces of the type typically exerted on the implant during chewing. The axially extending wall sections contribute significantly to the stability to radial loads and shear forces. In this design, the sealing collar is appropriately provided, in its top area, with a circumferential bevel on the inside and/or the outside. This bevel facilitates placing the post on the base body. The bevel automatically guides and centers the post relative to the base body.

An advantageous embodiment of the implant according to the invention results from the fact that the sealing collar is shaped flat at the front end. This flat design of the sealing collar at the front end makes for a contact face between the base body and the post that is transversely oriented relative to the longitudinal direction of the implant. This contact face greatly contributes to the stability of the connection, as the face, which is oriented transversely to the longitudinal direction of the implant, can transmit, without difficulty, the substantial pressures that act on the implant in longitudinal direction during chewing.

In another preferred embodiment of the invention the annular groove is tapered toward its bottom. In an especially preferred design, the annular groove, when viewing in the longitudinal direction of the implant, tapers conically toward its bottom. The conically tapering design of the annular groove, in combination with the complementary shape of the post, creates a force fit between the post and the base body. So—during the implantation procedure—the post can initially be slid on to the base body. The conical design of the annular groove makes sure that the post will initially adhere to the base body without the need for further aids or tools. This is especially advantageous if the implant is placed in the upper jawbone. Due to the self-locking force fit between the post and the base body, the post cannot come off from the base body placed in the upper jawbone. This significantly facilitates the implantation procedure. Furthermore, the force fit provides a better seal, thus preventing the development of microgaps between the base body and the post.

Furthermore, it is advantageous to design the annular groove of the implant according to the invention in such manner that its bottom is flat. The flat design of the bottom of the annular groove results in a further contact face between the base body and the post that is transversely oriented relative to the longitudinal direction of the dental implant. Forces acting on the implant in axial direction can be transmitted via this face. If, furthermore, as described above, the sealing collar of the implant according to the invention is shaped flat on its top, the implant has several contact faces on its top which extend transversely to the longitudinal direction of the implant, which contact faces are arranged with spaces between them in the longitudinal direction of the implant. This design further increases the implant's resistance to shear forces.

In a preferred design, the base body according to the invention is provided with a self-cutting thread on its external top surface facing the jawbone. Such a self-cutting thread permits the dental implant to be firmly placed in a tooth root cavity previously formed in the jawbone. In an especially preferred design, the self-cutting thread has a lower section and an upper section, wherein the core diameter of the self-cutting thread is smaller in the lower section than it is in the upper section and wherein the pitch of the self-cutting thread is larger in the lower section than it is in the upper section. It has become evident that such a self-cutting thread design ensures optimum primary stabilization of the implant while reducing the pressures in the transition area between the sponge and cortical bone. For this purpose, the distance from the transition between the upper and the lower sections of the self-cutting thread to the top of the base body should be 2 to 4 mm, preferably approx. 2.5 mm.

The implant according to the invention, i.e. the base body and/or the post of the implant, is/are usually made of titanium—either pure or alloyed titanium. Titanium has proved to be a suitable material for osseointegration. Titanium and bone tissue are well compatible with each other, which makes sure that osseointegration usually proceeds quickly and without problems.

On the other hand, the compatibility of titanium with epithelial tissue and gingival connective tissue is less good. Here the healing and integration process may be delayed and complications may develop, such as perioimplantitis and plaque accumulation. It is desirable that in-healing of the gingival part of the implant should not take longer than the osseointegration process. It is known that epithelial and connective tissues are well compatible with ceramic materials, in particular with zirconium oxide. For this reason, it may be expedient to provide the base body and/or the post of the dental implant according to the invention with an external coating of zirconium oxide, preferably stabilized zirconium oxide. An especially preferred variant consists in coating the post of the implant with zirconium oxide. Stabilized zirconium may contain up to 10% w/w of yttrium oxide to counteract decomposition due to moisture. Where appropriate, the coating may contain aluminum oxide as well. Using in particular the cathode sputtering method, a zirconium oxide coating can be applied, with good adherence, to the metal of the base body and/or the post of the dental implant according to the invention. In the cathode sputtering process, material is removed from a cathode (target) and precipitates on a substrate. The coating process takes place in a vacuum chamber in the presence of an inert gas, such as argon. Reactive sputtering allows a further gas to be introduced, which reacts with the ions removed from the target.

BRIEF DESCRIPTION OF THE DRAWINGS

Below is a detailed description of an embodiment example of the invention based on the drawings.

DETAILED DESCRIPTION OF THE INVENTION

Figure 1:
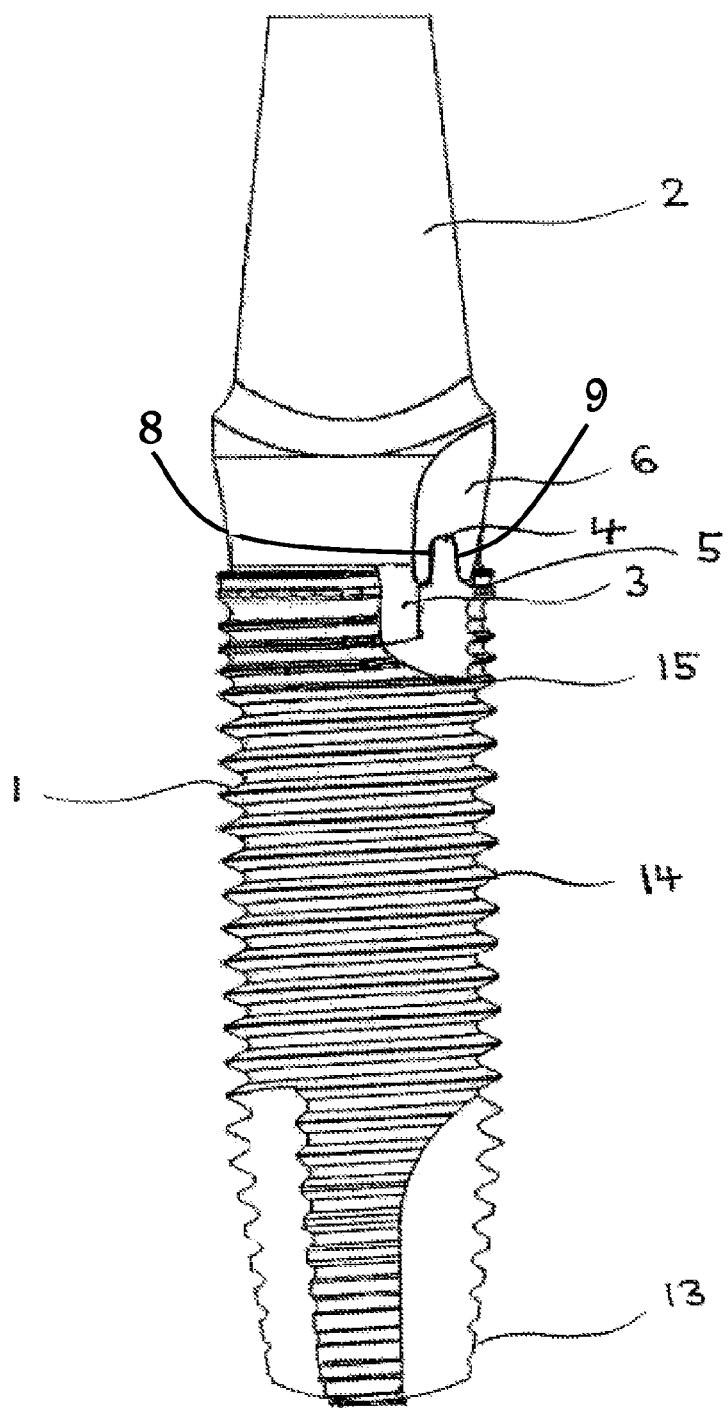
FIG. 1 is a partially cut top view of an embodiment example of the dental implant according to the invention.

The drawings show a dental implant for anchoring a prosthesis in the jaw of a patient. The implant comprises a base body 1 and a post 2 connecting to the top thereof. In the embodiment example shown, the base body 1 and the post 2 are made of titanium, with the post 2 being coated with zirconium oxide, which is the reason why the post 2 is lighter in color.

The post 2 engages with the recess opening 3 of the base body 1. The post 2 is secured to the base body 1 by means of a screw (not shown specifically in the drawings) which runs through the hollow post 2. The screw head is accessible at the top of the post 2.

On the top of the base body 1, there is sealing collar 4 surrounding the recess opening 3. The sealing collar 4 is surrounded by an annular groove 5. The post 2 has a circumferential shoulder 6 on its bottom facing the base body 1, which shoulder has a shape that is complementary to that of the sealing collar 4 and the annular groove 5.

Figure 2:
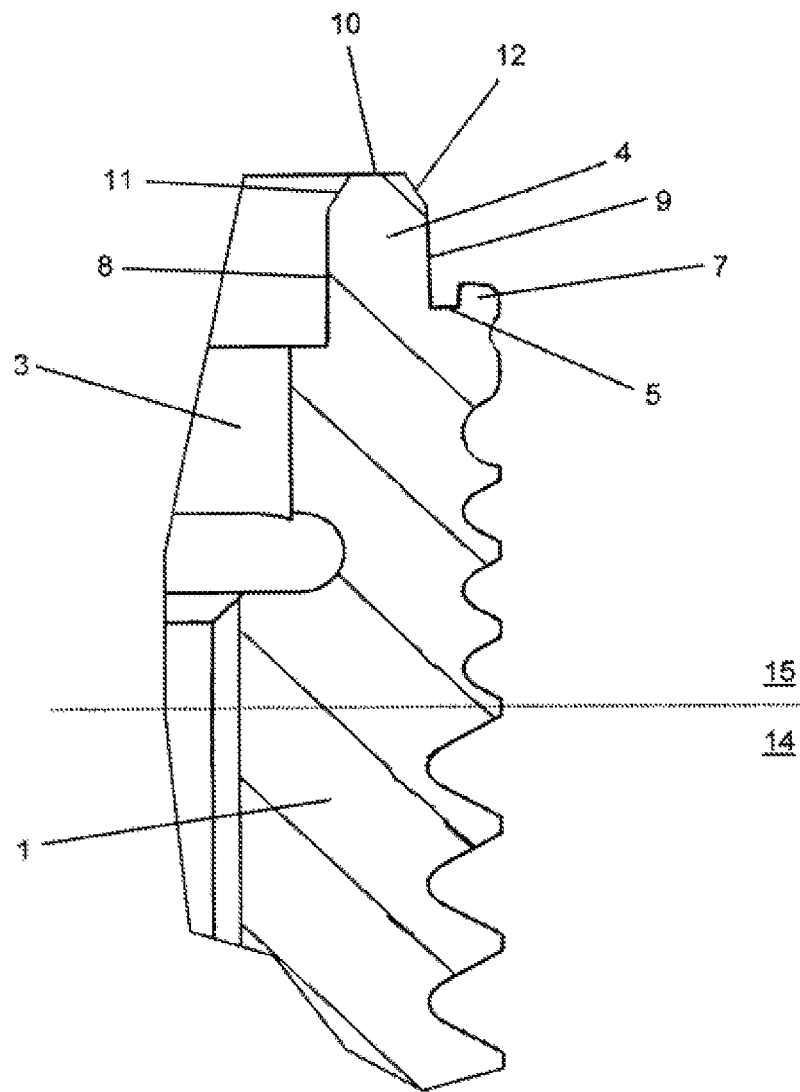
FIG. 2 is a partial cross-sectional representation of the base body of the dental implant according to the invention which shows the top area of the base body.

As can be seen in FIG. 2, an annular projection 7 directly adjoins the annular groove 5 in radial direction. If the implant according to the invention is designed as a subgingival implant, the top edge of the base body 1 implanted in the jawbone is level with the jawbone. The effect of the projection 7 is that the material of post 2 (not shown in FIG. 2) is set back toward the interior at the bottom of the post 2. Thus the surface of the post 2 does not come into contact with the bone. This prevents bone resorption in the transition area between the base body 1 and the post 2.

In the embodiment example shown in the drawings, the sealing collar 4, when viewing in the longitudinal direction of the implant, is web-shaped in cross section and has an axially extending inner wall 8 and an outer wall 9 that is almost parallel to the former. The sealing collar 4 is shaped flat at its front end 10, which results in a contact face between the base body 1 and the post 2 that extends transversely to the longitudinal direction of the implant. On the inside and on the outside, i.e. in the transition area between the wall 8 and the front end 10 and/or between the wall 9 and the front end 10, the sealing collar 4 is provided with a circumferential bevel 11 and/or 12, as can be seen in FIG. 2.

The annular groove 5 is conically tapered toward its bottom, with the bottom of the annular grove 5 being flat. Due to the conical taper of the annular groove 5 and the complementary shape of the post 2, a force fit is created between the post 2 and base body 1. This results in a sealed force fit between the base body 1 and the post 2, which effectively prevents migration of microorganisms in the contact area between the base body 1 and the post 2.

As can be seen from FIG. 1, the base body 1 is provided with a self-cutting thread on its outer surface facing the jawbone. On the bottom side of the base body 1, there are specially shaped cutting edges 13 which ensure that the screw-in torque for the base body 1 remains constant during the implantation procedure.

The self-cutting thread has a lower section 14 and an upper section 15, wherein the core diameter or the base thread diameter of the self-cutting thread is smaller in the lower section 14 than it is in the upper section 15. For example, the core diameter of the self-cutting thread is 0.175 mm larger in the upper section 15 than it is in the lower section 14. In addition, the pitch of the self-cutting thread is smaller in the upper section 15 than it is in the lower section 14. For example, the thread pitch in the upper section 15 is 0.2 mm smaller than it is in the lower section 14. In the embodiment shown, the distance from the transition between the upper section 15 and the lower section 14 to the top of the base body 1, i.e. the top of the projection 7, is approx. 2.5 mm. The design of the self-cutting thread shown makes for optimum primary stabilization of the implant, while reducing the pressures in the transition area between the sponge and cortical bone.

The invention claimed is:

1. An implant for anchoring a dental prosthesis in the jaw of a patient, having a base body (1) and a post (2) connecting to the top thereof and intended to be connected to the base body (1) by means of a screw, wherein the post (2) engages with a recess opening (3) of the base body (1) in a positive and non-positive manner and can be firmly connected thereto, characterized in that a sealing collar (4) surrounding the recess opening (3), an annular groove (5) surrounding the sealing collar (4), and an annular projection (7) extending axially and surrounding the annual groove (5) in radial direction, the annular groove (5) being conically tapered towards its bottom, are provided on the top of the base body (1), wherein the post (2) has a circumferential shoulder (6) on the bottom thereof facing the base body (1), the shoulder having a shape that is complementary to the sealing collar (4) and the annular groove (5), wherein the sealing collar (4), when viewing in the longitudinal direction of the implant, is web-shaped in cross section and has an axially extending inner wall (8) and an outer wall (9) that is essentially parallel to the former, the sealing collar being provided, at its top, with a circumferential bevel (11) on the inside and a circumferential bevel (12) on the outside.

2. The implant according to claim 1, characterized in that the sealing collar (4) is shaped flat at its front end (10).

3. The implant according to claim 1, characterized in that the annular groove (5) is shaped flat on its bottom.

4. The implant according to claim 1, characterized in that the base body (1) has a self-cutting thread on its outer surface facing the jawbone.

5. The implant according to claim 4, characterized in that the self-cutting thread comprises a lower section (14) and an upper section (15), wherein the core diameter of the self-cutting thread is smaller in the lower section (14) than it is in the upper section (15) and wherein the pitch of the self-cutting thread is larger in the lower section (14) than it is in the upper section (15).

6. The implant according to claim 5, characterized in that the distance from the transition between the upper and lower sections (14, 15) of the self-cutting thread to the top of the base body (1) is 2 to 4 mm, preferably approx. 2.5 mm.

7. The implant according to claim 1, characterized in that the base body (1) and/or the post (2) is/are made of titanium or a titanium alloy.

8. The implant according to claim 1, characterized in that the base body (1) and/or the post (2) is/are externally coated with zirconium oxide.

* * * * *